United States Patent
Wade et al.

(10) Patent No.: US 10,481,024 B2
(45) Date of Patent: Nov. 19, 2019

(54) PRESSURE SENSOR ASSEMBLY INCLUDING A CURED ELASTOMERIC FORCE TRANSMITTING MEMBER

(71) Applicant: Honeywell International Inc., Morris Plains, NJ (US)

(72) Inventors: Richard Wade, Worthington, OH (US); Brian Speldrich, Freeport, IL (US); Richard C. Sorenson, Columbus, OH (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 163 days.

(21) Appl. No.: 15/492,874

(22) Filed: Apr. 20, 2017

(65) Prior Publication Data

US 2018/0306660 A1    Oct. 25, 2018

(51) Int. Cl.
*G01L 9/00* (2006.01)
*G01L 19/00* (2006.01)
(Continued)

(52) U.S. Cl.
CPC ......... *G01L 9/0048* (2013.01); *A61M 5/1452* (2013.01); *A61M 5/14244* (2013.01);
(Continued)

(58) Field of Classification Search
CPC . G01L 9/0048; G01L 9/06; G01L 7/08; G01L 7/00; G01L 19/0069;
(Continued)

(56) References Cited

U.S. PATENT DOCUMENTS 6,229,190 B1 * 5/2001 Bryzek ................. G01L 9/0042
257/254
6,311,561 B1    11/2001 Bang et al.
(Continued)

FOREIGN PATENT DOCUMENTS

DE    102011013912 A1    9/2012
EP       2474819 A1    7/2012
(Continued)

OTHER PUBLICATIONS https://www.protolabs.com/services/injection-molding/liquid-silicone-ru . . . , "Liquid Silicone Rubber Molding," Proto Labs, 4 pages, printed May 15, 2017.
(Continued)

*Primary Examiner* — Harshad R Patel
*Assistant Examiner* — Nigel H Plumb
(74) *Attorney, Agent, or Firm* — Alston & Bird LLP (57) ABSTRACT

Embodiments relate generally to a sensor device, method, and system are provided for housing a sensor. A pressure sensor assembly having a printed circuit board (PCB) with a pressure sensor and a ring mounted on the PCB. The pressure sensor assembly may include a force transmitting member positioned at least partially within the ring. The force transmitting member may transfer a force applied to a front side of the force transmitting member to a front side of the pressure sensor. A reservoir includes an extension that define an opening. The first side of the force transmitting member is exposed to the interior of the reservoir. The extension engages the first side of the force transmitting member to seal the opening.

20 Claims, 11 Drawing Sheets

(51) Int. Cl.
*A61M 5/145* (2006.01)
*A61M 5/168* (2006.01)
*A61M 5/142* (2006.01)
*G01L 19/06* (2006.01)

(52) U.S. Cl.
CPC ..... *A61M 5/16831* (2013.01); *G01L 19/0069* (2013.01); *G01L 19/0654* (2013.01); *A61M 2005/16863* (2013.01); *A61M 2205/3331* (2013.01)

(58) Field of Classification Search
CPC ........... G01L 19/0654; A61M 5/14244; A61M 5/1452; A61M 5/16831; A61M 2005/16863; A61M 2005/331; A61B 17/135
See application file for complete search history.

(56) References Cited

U.S. PATENT DOCUMENTS

| | | | |
|---|---|---|---|
| 6,393,922 B1 * | 5/2002 | Winterer | G01L 19/0084 73/754 |
| 6,441,503 B1 | 8/2002 | Webster | |
| 6,512,255 B2 | 1/2003 | Aoki et al. | |
| 6,877,380 B2 | 4/2005 | Lewis | |
| 6,885,291 B1 * | 4/2005 | Pollack | B60C 23/0433 116/34 R |
| 6,923,069 B1 | 8/2005 | Stewart | |
| 7,077,008 B2 * | 7/2006 | Pham | G01L 19/143 73/716 |
| 7,082,835 B2 | 8/2006 | Cook et al. | |
| 7,216,547 B1 | 5/2007 | Stewart et al. | |
| 7,260,994 B2 * | 8/2007 | Oboodi | G01L 9/0055 361/283.1 |
| 7,493,822 B2 | 2/2009 | Stewart et al. | |
| 7,503,221 B2 | 3/2009 | Wade | |
| 7,811,123 B2 | 10/2010 | Hoath et al. | |
| 8,024,978 B2 | 9/2011 | Khemet et al. | |
| 8,061,212 B2 | 11/2011 | Shubert | |
| 8,230,743 B2 * | 7/2012 | Wade | G01L 9/0052 73/706 |
| 8,371,176 B2 * | 2/2013 | Rozgo | G01L 19/0007 73/756 |
| 2003/0167851 A1 | 9/2003 | Parker | |
| 2007/0235083 A1 * | 10/2007 | Dlugos | A61F 5/0003 137/223 |
| 2011/0214504 A1 * | 9/2011 | Bradley | A61M 39/08 73/723 |

FOREIGN PATENT DOCUMENTS

| | | | |
|---|---|---|---|
| JP | 2006220456 A1 | | 8/2006 |
| JP | 2016212015 | * | 12/2016 |
| JP | 2016212015 A1 | | 12/2016 |
| WO | 0042405 A1 | | 7/2000 |

OTHER PUBLICATIONS

Measurement Specialties, "MS5535-30C 30 Bar Pressure Sensor Module" Available at www.meas-spec.com, 21 pages, Jun. 27, 2011.
Measurement Specialties, "MS5536-30C SMD Gage Pressure Module," Available at www.meas-spec.com, 18 pages, Jun. 27, 2011.
Measurement Specialties, "MS5541-30C Miniature 30 Bar Module," Available at www.meas-spec.com, 21 pages, Jun. 27, 2011.
Measurement Specialties, "RoHS 1620," Available at www.meas-spec.com, 6 pages, May 2012.
Measurement Specialties, "RoHS 1630," Available at www.meas-spec.com, 5 pages, Jun. 2011.
Extended European Search Report, Application No./Patent No. 181675301-3392634, pp. 12, dated Jan. 22, 2019.
Non-Final Rejection dated Aug. 2, 2019 for U.S. Appl. No. 15/684,061.

* cited by examiner

PRESSURE SENSOR ASSEMBLY INCLUDING A CURED ELASTOMERIC FORCE TRANSMITTING MEMBER

TECHNICAL FIELD

The present disclosure relates generally to sensors, and more particularly to pressure sensor assembly structures.

BACKGROUND

Pressure sensors are used today to sense pressure in a wide variety of applications including, for example, medical applications, flight control applications, industrial process applications, combustion control applications, weather monitoring applications, water metering applications, as well as many other applications. Integrating such pressure sensors into a system can present certain challenges. What would be desirable is a cost effective pressure sensor that can be easily integrated into a system, such as a medical system.

SUMMARY

The present disclosure relates generally to sensors, and more particularly to pressure sensor assemblies. The present disclosure describes various pressure sensor assemblies that can be produced in a cost effective manner and can be easily integrated into a system, such as a medical system.

In one example, a pressure sensor assembly may include a printed circuit board, a pressure sensor, and a force transmitting member. The printed circuit board may have a front side and a back side. The pressure sensor may have a front side and a back side, and the pressure sensor may be mounted to the printed circuit board with the back side of the pressure sensor facing the front side of the printed circuit board. The force transmitting member may have a front side and a back side, and the back side of the force transmitting member may engage the front side of the pressure sensor such that the force transmitting member may transmit a force applied to the front side of the force transmitting member to the front side of the pressure sensor. In some cases, the force transmitting member may be or may include an elastomer, such as cured silicone elastomer.

In some instances, the pressure sensor assembly may include a ring (e.g., a support ring). The ring may have a front side and a back side, and the ring may be mounted to the printed circuit board with the back side of the ring facing the front side of the printed circuit board and the front side of the ring may be spaced away from the front side of the printed circuit board. The ring may extend circumferentially around the pressure sensor and may define an opening from the front side of the ring to the pressure sensor. In some cases, the force transmitting member may be at least partially received within the opening defined by the ring. In some instances, the force transmitting member may extend beyond the front side of the ring. In some cases, the front side of the force transmitting member may be domed shaped.

The disclosed pressure sensor assemblies may be used in a variety of applications. In some instances, the pressure sensor assembly may be used in conjunction with a reservoir that is configured to contain a fluid (e.g., gas or liquid), such as a medicament or other fluid. The reservoir may include an opening that extends to an interior of the reservoir. The pressure sensor assembly may be positioned within the opening such that the pressure sensor (e.g., via the force transmitting member) may be exposed to the interior of the reservoir for sensing a pressure in the interior of the reservoir. In some instances, the force transmitting member may form a seal that seals the opening in the reservoir.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following description of various illustrative embodiments of the disclosure in connection with the accompanying drawings, in which.

While the disclosure is amenable to various modifications and alternative forms, specifics thereof have been shown by way of example in the drawings and will be described in detail. It should be understood, however, that the intention is not to limit aspects of the disclosure to the particular embodiments described herein. On the contrary, the intention is to cover all modifications, equivalents, and alternatives falling within the spirit and scope of the disclosure.

DESCRIPTION

The following description should be read with reference to the drawings wherein like reference numerals indicate like elements throughout the several views. The description and drawings show several embodiments which are meant to be illustrative of the disclosure.

Figure 1:
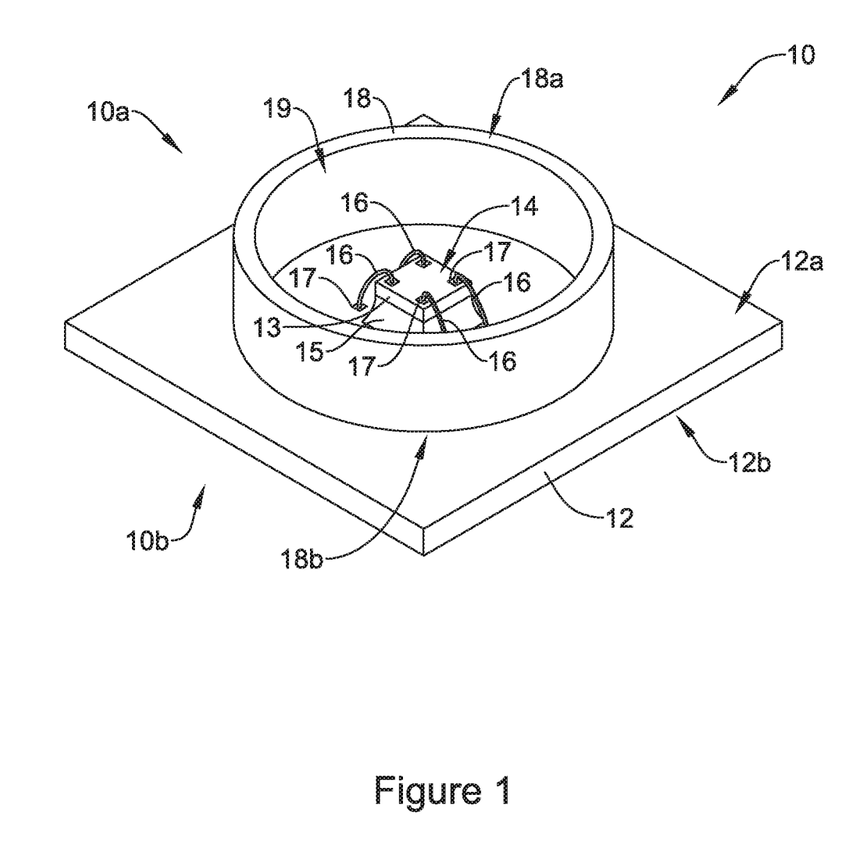
FIG. 1 is a schematic perspective view of an illustrative sensor assembly with the force transmitting member removed.

FIG. 1 is a schematic perspective view of an illustrative sensor assembly with the force transmitting member removed. The illustrative sensor assembly 10 (e.g., a sensing unit) may have a first side 10a and a second side 10b, a printed circuit board (PCB) 12 having a first side 12a (e.g., a front side) and a second side 12b (e.g., a second side), a pressure sensor 14 mechanically and/or electrically connected to the PCB 12 (e.g., via wire bonds, solder, adhesive, and/or other connection), a support ring 18 having a first side 18a (e.g., a front side) and a second side 18b (e.g., a back side), and/or one or more other components. Although not shown in FIG. 1, an insert (e.g., a media isolation layer and/or a force transmitting member or material) may fill or at least partially fill the support ring 18 and encapsulate the components within a cavity 19 or opening defined by the support ring 18.

The PCB 12 of the pressure sensor assembly 10 may be any type of PCB. In some cases, the PCB 12 may be a thick film printed ceramic board, but this is not required. In one example, the PCB may be made, at least in part, of FR 4 laminate and/or other material.

Although not particularly detailed in the Figures, the PCB 12 may have one or more electronic components thereon and/or pads for connecting to electronic components of a device in which the pressure sensor assembly 10 may be inserted or with which the pressure sensor assembly 10 may be used. In one example, the PCB 12 may include an application specific integrated circuit (ASIC) that may be attached to the first side 12a or the second side 12b of the PCB 12. Such an ASIC may be electrically connected to the PCB 12 via wire bonds, bump bonds, electrical terminals, and/or any other suitable electrical connections. Additionally or alternatively, the PCB may include one or more conductive pads for engaging circuitry and/or electronic components in communication with a remote processor or the like.

Further, the PCB 12 may include one or more processing electronics and/or compensation circuitry (e.g., which may or may not include an ASIC). Such processing electronics may be electrically connected to terminals of the pressure sensor 14, an ASIC (if present), and/or electrical terminals to process electrical signals from the pressure sensor 14 and/or to transfer outputs from the pressure sensor 14 to electronic components of one or more devices used in conjunction with the pressure sensor assembly 10. In some instances, the PCB 12 may include circuitry that may be configured to format one or more output signals provided by the pressure sensor 14 into a particular output format. For example, circuitry of the PCB 12 (e.g., circuitry on one or more of the first side 12a and the second side 12b of the PCB 12) may be configured to format the output signal provided by pressure sensor 14 into a ratio-metric output format, a current format, a digital output format and/or any other suitable format. In some cases, the circuitry of the PCB 12 may be configured to regulate an output voltage. Circuitry on the PCB 12 for providing a ratio-metric (or other) output may include traces and/or other circuitry that may serve as a conduit to test pads, and/or for providing the ratio-metric (or other) output to one or more electrical terminals facilitating electrical connections with electronic components of one or more devices used with the pressure sensor assembly 10.

Figure 2:
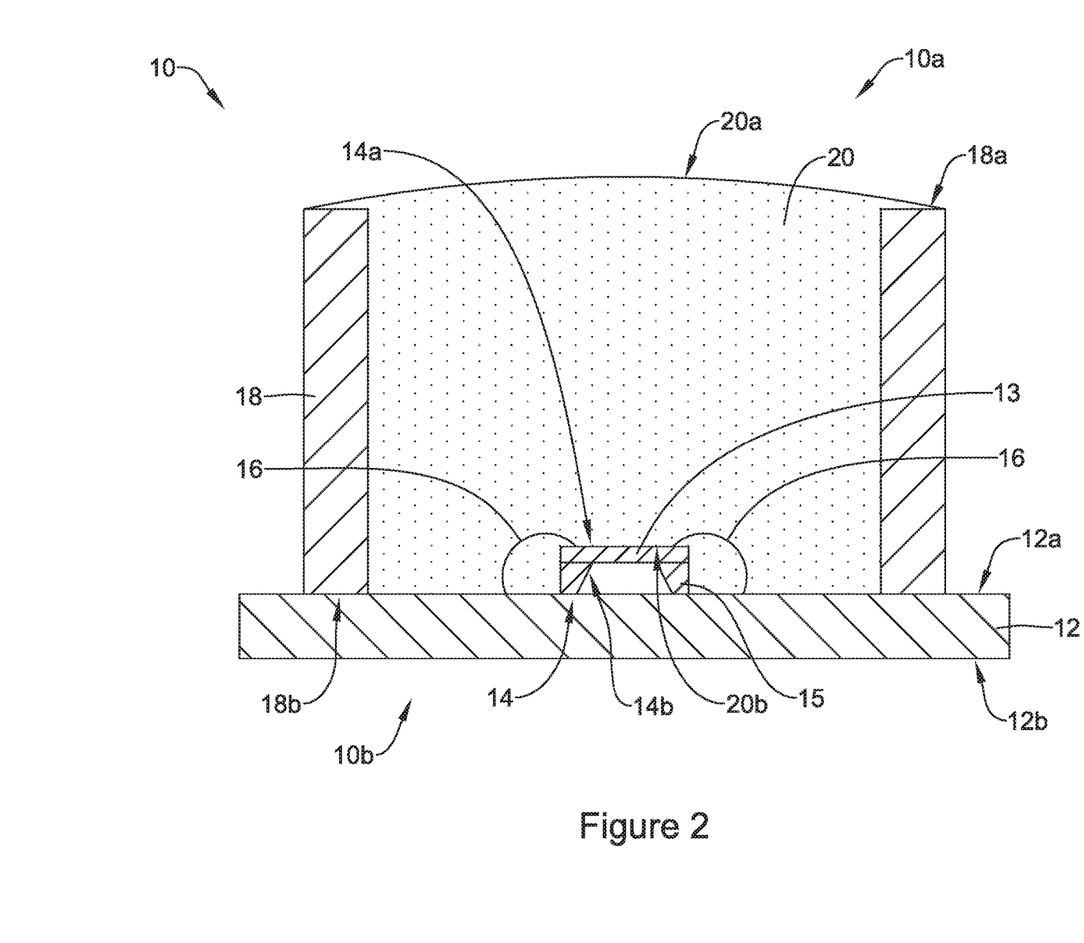
FIG. 2 is a schematic cross-section view of the illustrative sensor assembly of FIG. 1 with an illustrative force transmitting member.
Figure 3:
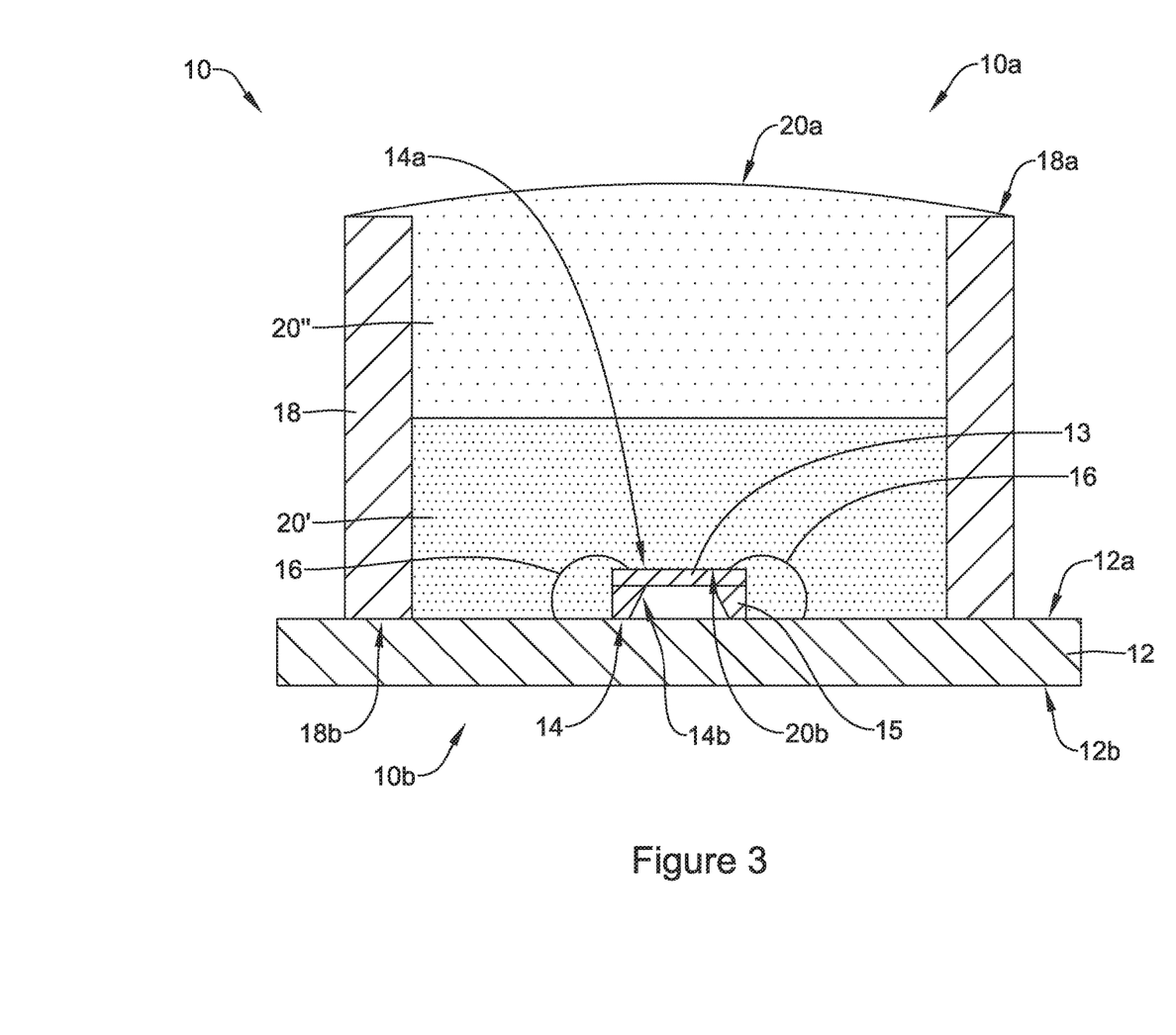
FIG. 3 is a schematic cross-section view of the illustrative sensor assembly of FIG. 1 with another illustrative force transmitting member.
Figure 4:
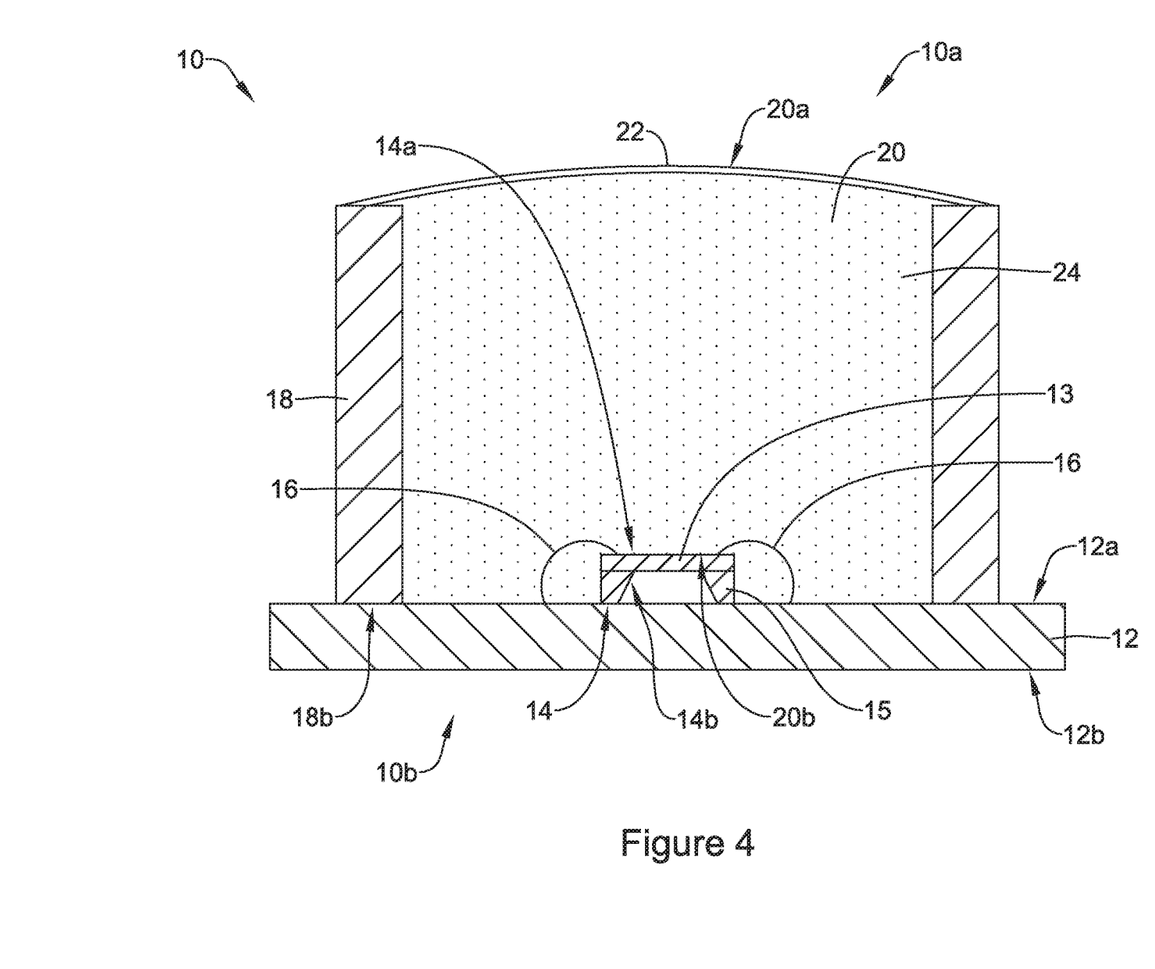
FIG. 4 is a schematic cross-section view of the illustrative sensor assembly of FIG. 1 with yet another illustrative force transmitting member.

The pressure sensor 14 of the pressure sensor assembly 10 may be configured in any manner and may have a first side 14a (e.g., a front side) and a second side 14b (e.g., a back side) (see FIGS. 2-4). In some cases, the pressure sensor 14 may include a micro-machined pressure sense die that includes a sense diaphragm. The pressure sense die may be secured directly to the PCB 12 and/or may be secured to a constraint 15 (as shown in FIG. 1), and the constraint 15 is secured to the PCB 12. The constraint 15, when included, may help isolate the pressure sense die from stresses induced by the PCB 12 and/or packaging in which the pressure sensor 14 is mounted. The constraint 15 may be bonded, anodically or by other means, to the pressure sense die 13. The constraint 15 may be made of any material. In some cases, the constraint 15 may made of glass, silicon, or other material.

In some cases, the pressure sensor 14 may be back-side mounted on the first side 12a of the PCB 12 with the second side 14b of the pressure sensor 14 facing the first side 12a of the PCB 12 and may be configured to perform top-side sensing (e.g. sensing with the first side 14a of the pressure sensor 14). In a pressure sensor configuration, the top-side sensing may be when a sensed media either directly or indirectly (e.g., through the force transmitting member 20 or other intermediary) interacts with a top side of the pressure sensor 14, where a back- or bottom-side of the pressure sensor 14 may be etched inward toward the top-side to form a sensing diaphragm.

Back-side mounting the pressure sensor 14 to the first side 12a of the PCB 12 may facilitate creating a robust pressure sensor assembly 10, where the first side 12a (e.g., the front side) may be configured to face an interior of a reservoir and/or a location of sensed media. In one example, back-side mounting the pressure sensor 14 to the first side 12a of the PCB 12 may create a more robust pressure sensor assembly 10 because any sensed media acting on the pressure sensor 14 may act to push the pressure sensor 14 against the PCB 12. Additionally, such a configuration may allow for a smaller pressure sensor 14 when compared to sensor units in which a pressure sensor 14 may be mounted to the second side 12b of the PCB 12 that faces away from an interior of the reservoir and/or a location of sensed media. Such a smaller pressure sensor 14 may be possible, at least in part, because less sense element surface area is needed to attached the pressure sensor 14 to PCB 12 when the pressure sensor 14 is connected to the first side 12a of the PCB 12 facing the interior of a reservoir and/or a location of sensed media due to forces from the interior of the reservoir and/or a location of sensed media pushing the pressure sensor 14 into the PCB 12 instead of pushing the pressure sensor 14 away from the PCB 12.

Although the pressure sensor 14 may be described herein as being back-side mounted to the first side 12a of the PCB 12, it is contemplated that the pressure sensor 14 may be mounted relative to the PCB 12 in one or more other configurations. For example, the pressure sensor 14 may be front side mounted, and/or the pressure sensor 14 may be mounted in any other suitable manner.

The pressure sensor 14 may be electrically connected to the PCB 12 in one or more manners. In one example, wire bonds 16 may be utilized to electrically connect the pressure sensor 14 to the PCB 12. In such a case, the wire bonds 16 may have a first end connected to a bond pad 17 of the pressure sensor 14 and another end connected to a bond pad 17 of the PCB 12. Additionally or alternatively, the pressure sensor 14 may be electrically connected to the PCB via bump bonds and/or in any other suitable manner.

The micro-machined pressure sense die of the pressure sensor 14 may have any size or shape. In some cases, the pressure sense die may have a thickness between about 200 microns and about 800 microns and a surface area between about 10,000 microns$^2$ and about 4,000,000 microns$^2$. In some examples, the pressure sense die may have a thickness dimension between about 380 microns and about 410 microns and a surface area between about 200,000 microns$^2$ and about 500,000 microns$^2$. In one example, the pressure sense die may have a thickness dimension of about 390 microns and a surface area of about 390,625 microns$^2$ (e.g., when the pressure sense die is rectangular or square, the pressure sense die may have edges of about 625 microns in length).

The pressure sense die of the pressure sensor 14 may be arranged to sense an absolute pressure, where a pressure of fluid in the reservoir 30 is referenced against a vacuum pressure or other reference pressure. When sensing an absolute pressure, the pressure sense die 13 and/or the constraint 15 may be fabricated to include a vacuum or reference cavity immediately behind a sense diaphragm, such that a pressure of fluid in the reservoir 30 is referenced against a vacuum (not specifically shown) or other reference pressure. Alternatively, the pressure sense die may be arranged to sense a gauge pressure. In such a gauge pressure sensor, the PCB 12 and/or the constraint 15 may include an opening extending from the pressure sense die 13 through the PCB 12 (e.g., extending through the PCB 12 from the first side 12a to the second side 12b of the PCB 12) to allow a reference pressure to reach the back side of the pressure sense die 13. Example pressure sensor die may include, but are not limited to, those described in U.S. Pat. Nos. 7,503,221; 7,493,822; 7,216,547; 7,082,835; 6,923,069; 6,877,380, and U.S. patent application publications: 2010/0180688; 2010/0064818; 2010/00184324; 2007/0095144; and 2003/0167851, all of which are hereby incorporated by reference.

In some cases, the support ring 18 of the pressure sensor assembly may entirely or at least partially circumferentially surround and/or enclose the pressure sensor 14, wire bonds 16, bond pads 17, the force transmitting member 20, and/or other components of the pressure sensor assembly 10. The support ring 18 may have a circular cross-section, but this is not required and the support ring 18 may take on one or more shapes having a circular cross-section and/or a different shaped cross-section.

The support ring 18 may be connected to the first side 12a of the PCB 12 such that the second side 18b of the support ring 18 may face the first side 12a of the PCB 12 and the first side 18a of the support ring 18 may be spaced away from the first side 12a of the PCB 12. In some cases, the support ring 18 may be attached to at least a portion of the first side 12a of the PCB 12 to provide additional support that adds structural integrity to the pressure sensor assembly 10. The first side 18a of the support ring 18 may at least partially define an opening from the first side 18a of the support ring 18 to the pressure sensor 14 (e.g., the cavity 19 defined by the support ring 18). The support ring 18 may be made from any type of material. In one example, the support ring 18 may be made from a plastic, a metal, a ceramic and/or any other suitable material.

In some cases, an attach or adhesive may be used to mechanically and/or electrically connect one or more of the pressure sensor 14, the support ring 18 and/or other components of the pressure sensor assembly 10 to the first side 12a of the PCB 12. The adhesive may be a single piece or layer of adhesive, or may include two or more pieces or layers of adhesive. The adhesive may be any adhesive capable of facilitating assembly of the pressure sensor assembly 10, such as an epoxy adhesive or other similar or different adhesives. Illustrative adhesives may include, but are not limited to, an adhesive having the ingredients of at least Bisphenol-A type epoxy resin, Diglycidyl ether of neopentyl glycol, cycloaliphatic/aliphatic amine, aluminum oxide, carbon black, and amorphous silicon dioxide; an adhesive having the ingredients of epoxy phenol novalac (25%-50% by weight), aluminum powder (10%-25% by weight), flexibilizer epoxy resin (10%-25% by weight), curing agent (2.5%-10% by weight), siloxane treated silicon dioxide (2.5%-10% by weight), silicon dioxide, chemically prepared (≤2.5% by weight), and curing agent (≤2.5% by weight); and an adhesive having the ingredients of epoxy resin (70%-90% by weight), non-volatile amide (10%-30% by weight) and amorphous silica (1%-5% by weight), or other suitable adhesives as desired.

FIGS. 2-4 depict cross-section views of a pressure sensor configuration of the pressure sensor assembly 10 with various configurations of a force transmitting member located at least partially within the opening or cavity 19 defined by the support ring 18. Although the pressure sensor assembly 10 may be depicted in FIGS. 2-4 as a gauge pressure sensor, the pressure sensor assembly 10 may be or may include any type of pressure sensor including an absolute pressure sensor.

In some cases, the support ring 18 may entirely or at least partially around the perimeter of the pressure sensor 14, wire bonds 16, the force transmitting member 20, and/or other components of the pressure sensor assembly 10. Further, the force transmitting member 20 may fill or at least partially fill the opening or cavity 19 of the support ring 18 to facilitate transferring a force interacting with the first side 20a (e.g., front side) of the force transmitting member 20 to the pressure sensor 14 and/or to protect components of the pressure sensor assembly 10 from the sensed media. In some cases, the force transmitting member 20 may have a first side 20a (e.g., a front side) and a second side 20b (e.g., a back side), where the first side 20a is configured to interact with a sensed media and the second side 20b interacts with the pressure sensor 14 such that at least some of the force (caused by pressure) acting on the first side 20a of the force transmitting member 20 is transferred to the second side 20b of the force transmitting member 20 and to the pressure sensor 14.

The force transmitting member 20 may be formed from one or more layers of material. For example, the force transmitting member 20 may be formed from one layer of material, two layers of material, three layers of material, four layers of material, five layers of material, or other number of layers of material.

The force transmitting member 20 may be made from any suitable material. Example types of material may include dielectric material, a non-compressible material, a biocompatible material, colored material, non-colored material, and/or one or more other types of material. Example materials acceptable for use as or in the force transmitting member 20 may include fluoro-silicone gel, a cured silicone rubber or silicone elastomer, a cured liquid silicone rubber, an oil and/or any other suitable material. In one example, the force transmitting member 20 may include a biocompatible material that is medically safe to directly contact medicines or the like that are to be provided to a patient. One such biocompatible material is a cured silicone elastomer. This is just one example.

Silicone elastomers are polysiloxanes and/or polydimethylsiloxanes. Example silicone elastomers may include SILASTIC® MDX4-421 Biomedical grade elastomer from Dow Corning Corporation, SILPURAN® 2430 (e.g., an addition curing RTV silicone rubber curing to a silicon elastomer) from Wacker Chemie AG, and/or one or more other silicone elastomers.

The force transmitting member 20 may be formed using any suitable technique. For example, the force transmitting member 20 may be formed with one or more of a molding technique, a curing technique, a mixing technique, a trimming technique, and/or one or more other techniques. In one example, a silicone elastomer liquid material may be inserted into the support ring 18 and then cured to cure the liquid material and cause it to solidify and maintain a shape at least partially defined by the support ring 18. In another example, the pressure sensor assembly 10, without the force transmitting member 20 and, optionally, without the gel ring 18, may be inserted into or onto a mold, a liquid material may be added to the mold and then cured. The mold may then be removed and the pressure sensor assembly 10 with the force transmitting member 20 may be formed. Further, in another example, an opening in a reservoir or other fluid container in which the pressure sensor assembly 10 may be located in an application may be utilized as a form or mold. In such cases, a piston arm or other feature of the reservoir or other occlusion may be advanced against one side of the opening, a liquid may be inserted into the opening, the pressure sensor assembly 10, without the force transmitting member 20 and, optionally, without the gel ring 18, may be positioned on or over the liquid in the opening, and then the liquid may be cured to form the force transmitting member 20 with or without a gel ring 18, which results in a pressure assembly 10 in a desired application.

In an example of when a silicone elastomer is used in forming the force transmitting member 20, a silicone elastomer may be provided in a mold, a gel ring, an opening of a reservoir, or other form and then cured to take the desired form. The silicone elastomer may be cured by, for example, an addition system (e.g., a platinum-catalyzed system), a condensation cure system, a peroxide cure system, an oxime cure system, heat and/or by otherwise curing the silicone elastomer.

FIG. 2 depicts a cross-section of the pressure sensor assembly 10 with the force transmitting member 20 formed from a single material, such as a cured silicone elastomer or other material, with the force transmitting member 20 configured to receive a force at the first side 20*a* and apply the received force to the first side 14*a* of the pressure sensor 14. In this case, as the cured silicone elastomer is a biocompatible material, the cured silicone elastomer may form a surface (e.g., the first side 20*a* of the force transmitting member 20) that can directly engage a sensed media such as a medicine in a medical application.

In some cases, the first side 20*a* of the force transmitting member 20 may be formed in a dome shape, as shown in FIG. 2, but this is not required in all cases. Although not necessarily required, when the first side 20*a* is domed and/or in other configurations, the dome shape of the first side 20*a* may extend to an edge of the gel ring 18 or other location along the first side 18*a* of the support ring 18.

Note, the dome shapes depicted throughout the Figures are not drawn to scale. In some cases, the actual dome shape is less domed than what is shown in the Figures.

A dome shape to the first side 20*a* of the force transmitting member 20 may have one or more benefits over a flat or a recessed first side 20*a* of the force transmitting member 20. For example, the dome shape may facilitate removal of a fluid from a reservoir (e.g., removal of all or substantially all medicament from a reservoir), may help create a seal between the pressure sensor assembly 10 and a reservoir, and/or may facilitate abutting a membrane if one is provided over the force transmitting member 20 without creating air bubbles between the membrane and the force transmitting member 20. When domed, and/or in other configurations, the first side 20*a* of the force transmitting member 20 may extend radially beyond an inner wall of the support ring 18 and may overlap the first side 18*a* of the support ring 18 as shown in FIG. 2.

FIG. 3 depicts a cross-section of the pressure sensor assembly 10 with a force transmitting member 20 formed from two layers of materials, such as a first layer 20' and a second layer 20". The first layer 20' and the second layer 20" may be any suitable materials for transferring a force applied to the first side 20*a* of the force transmitting member 20 to the second side 20*b* of the force transmitting member 20 and the pressure sensor 14. In one example, the second layer 20" may be or may include a biocompatible material, such as a cured silicone elastomer or other biocompatible material, and the first layer 20' may be a gel (e.g., a non-compressible gel such as a fluoro-silicone gel), oil, or other material. Other material may be used as desired and in some cases, a membrane may be utilized over the first side 20*a* of the force transmitting member 20, as shown in FIG. 4.

The first and second layers 20', 20" of the force transmitting member 20 may be arranged in any order and/or may have any thickness, as desired. As shown in FIG. 3, the second layer 20" of the force transmitting member 20 may be an outer layer of the force transmitting member 20 and may form at least part of the first side 20*a* of the force transmitting member 20, which may interact directly with a sensed media and/or indirectly with a sensed media via a membrane. Further, the first layer 20' of the force transmitting member 20 may be an inner layer of the force transmitting member 20 and may form at least part of the second side 20*b* of force transmitting member 20 (e.g., a part of the force transmitting member 20 that engages the first side 14*a* of the pressure sensor 14). The force transmitting member 20 may have one or more layers between the first layer 20' and the second layer 20" or the first layer 20' may abut the second layer 20' as shown in FIG. 3. In some cases, a force acting on the second layer 20" of the first force transmitting member 20 may be transferred to the first layer 20' (e.g., directly or through one or more layers of the force transmitting member 20) and applied to the pressure sensor 14 to measure a force (caused by a pressure) at the first side 20*a* of the force transmitting member 20. Additionally, as discussed above, the material of the force transmitting member 20 defining the first side 20*a* (e.g., the second layer 20") may be domed in a manner similar to as discussed above with respect to FIG. 2.

FIG. 4 depicts a cross-section of the pressure sensor assembly 10 with a force transmitting member 20 having a membrane 22 overlaying a primary material 24 of the force transmitting member 20. The primary material 24 may be one or more materials that are configured to transfer a force from the first side 20*a* of the force transmitting member 20 to the second side 20*b* of the force transmitting member 20 including, but not limited to, a cured silicone elastomer or other biocompatible material, a gel (e.g., a non-compressible gel such as a fluoro-silicone gel), oil, or other material. The material of the membrane 22 may be any type of material that is capable of interacting with a sensed media and will not taint the sensed media. In some cases, the membrane 22 may be formed from a cured silicone elastomer or other biocompatible material.

Similar to as discussed above, the first side 20*a* of the force transmitting member 20 may be formed in a dome shape, as shown in FIG. 4. Such a dome shape may be formed by the primary material 24, but this is not required in all cases, and imparted by the primary material 24 to the membrane 22. Such a dome shape at the first side 20*a* of the force transmitting member 20 may have similar benefits to those discussed above. In addition, a domed portion of the primary material 24 of the force transmitting member 20 may facilitate creating an air-tight (e.g., bubble free) boundary between the primary material 24 and the membrane 22 due to the primary material 24 applying a positive pressure to the membrane 22.

Figure 5:
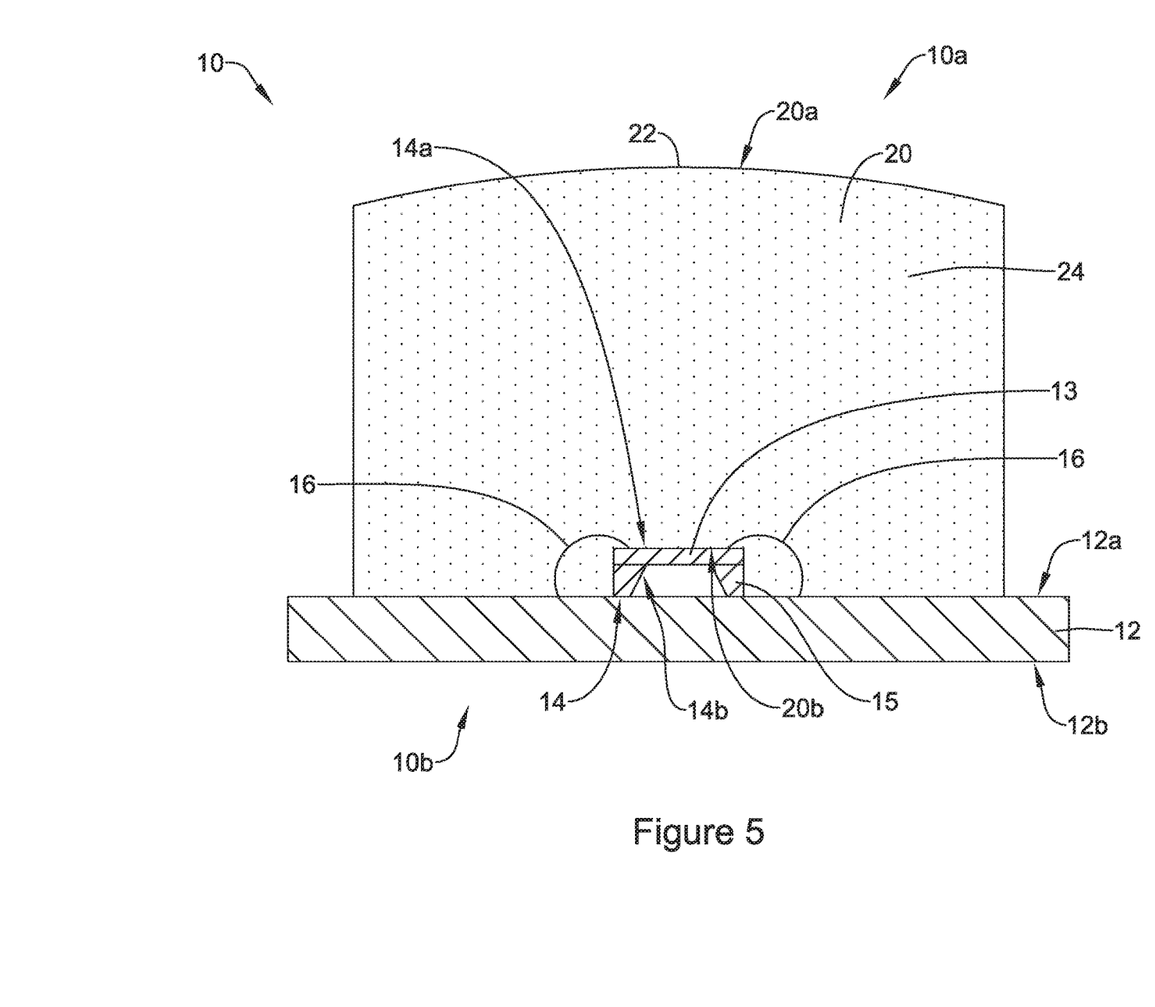
FIG. 5 is a schematic cross-section view of the illustrative sensor assembly of FIG. 1 with yet another illustrative force transmitting member.

FIG. 5 depicts a cross-section of the pressure sensor assembly 10 with the force transmitting member 20 formed from a single material, such as a cured silicone elastomer or other material, with the force transmitting member 20 configured to receive a force at the first side 20a and apply the received force to the first side 14a of the pressure sensor 14. In this case, the pressure sensor assembly 10 may not include the gel ring 18. Instead, the force transmitting member 20 may be formed by curing the silicone elastomer or other biocompatible material configured to transfer a force from the first side 20a to the second side 20b of the force transmitting member 20 in a mold or other from (e.g., an opening in a reservoir or other form) to give the force transmitting member 20 a desired shape. Although not depicted in FIG. 5, in some cases, the force transmitting member 20 may be formed from two or more materials and/or may include a membrane forming the first side 20a of the force transmitting member 20. Further, in some cases, the first side 20a of the force transmitting member 20 may be formed in a dome shape, as shown in FIG. 5, but this is not required in all cases.

The pressure sensors and/or pressure sensor assemblies (e.g., the pressure sensor assembly 10) disclosed herein may be used in one or more applications. For example, pressure sensors and/or pressure sensor assemblies, including those disclosed herein, may be used in medical applications, flight control applications, industrial process applications, combustion control applications, weather monitoring applications, water metering applications, as well as many other applications. In one example application, pressure sensors and/or pressure sensor assemblies may be used to directly sense pressure within a reservoir containing medicament for a patient. Although the pressure sensors and/or pressure sensor assemblies disclosed herein may be described primarily with respect to medicament-containing reservoirs, the pressure sensors and pressure sensor assemblies may be used in other applications as desired.

Patients with a disease or other medical issue may need to supplement their body with one or more medicaments (e.g., insulin, chemotherapy drugs, pain drugs, and/or other medicaments). Although medicaments may be provided via oral ingestion, shots, intravenous (IV) drips, and/or other techniques, patients are increasingly interested in portable and/or wearable pumps with which medicament may be self-administered. In some cases, portable and/or wearable pumps are or include components that are disposable (e.g., are meant to be disposed after a short time period or low number of uses (e.g., after one day, two days, three days, one week, one month or other time period and/or after a single use, after a reuse, after two reuses, after three reuses, after five reuses or after one or more other number of uses)) and meant to be replaced. Further, portable and/or wearable pumps may include a reservoir for holding medicament or other fluid, which may be disposed of with the portable and/or wearable pumps or may be disposed of separately from the portable and/or wearable pumps. Additionally or alternatively, portable and/or wearable pumps may be utilized for non-medical purposes.

Portable and wearable pumps may be configured to detect occlusion events, during which medicament or other fluid being outputted from a reservoir is blocked or partially blocked. The portable and wearable pumps may not use a dedicated pressure sensor to detect an occlusion event based on pressure in an interior of a reservoir, but instead may measure an electrical current that is applied to the pump's drive system. In some cases, where a motor is used to pump fluid out of a reservoir, a measurement of current draw by the motor may be utilized to approximate the pressure within a reservoir and identify when an occlusion event is taking place. This method, however, may lack reliability and may result in false positives whenever mechanical friction (e.g., when not caused by an occlusion) may resist the motion caused by the motor in a manner that cannot be distinguished from an occlusion event. This may be particularly problematic as portable and/or wearable pumps may ask a patient to replace the pump when an occlusion is detected and thus, false positive detection of occlusions may result in wasting pumps, reservoir components of pumps, medicament still in the pump, time, and/or other detriments.

Figure 6:
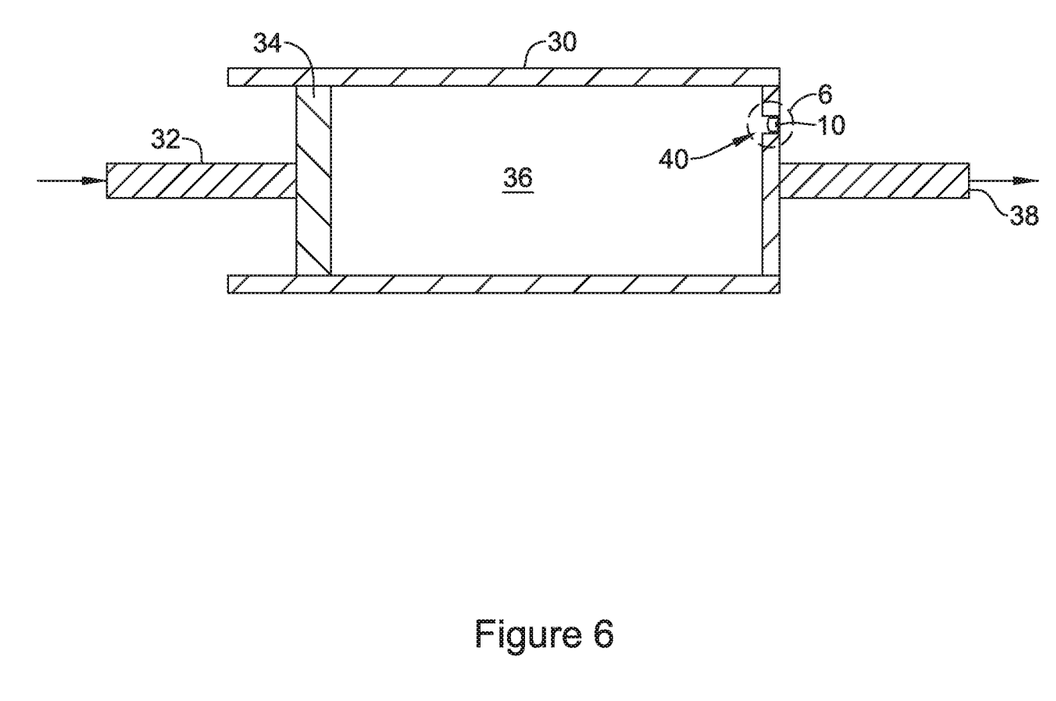
FIG. 6 is a schematic cross-section view of an illustrative reservoir including an illustrative pressure sensor assembly.

FIGS. 6-11 depict the pressure sensor assembly 10 in a medicament dispensing application. FIG. 6 depicts a cross-section of a reservoir 30 with a piston arm 32 of a medicament dispensing pump (not shown) driving a piston 34 down the reservoir 30. The reservoir 30 may include an interior 36 for receiving medicament and an outlet 38 for outputting medicament from the interior 36 as the piston 34 is advanced toward the outlet 38. In some cases, the reservoir 30 may include a port or opening 40 that may extend through a wall of the reservoir 30 between the ambient and the interior 36 of the reservoir. In some cases, the pressure sensor assembly 10 may be configured to be positioned within the opening 40 and secured therein.

Figure 7:
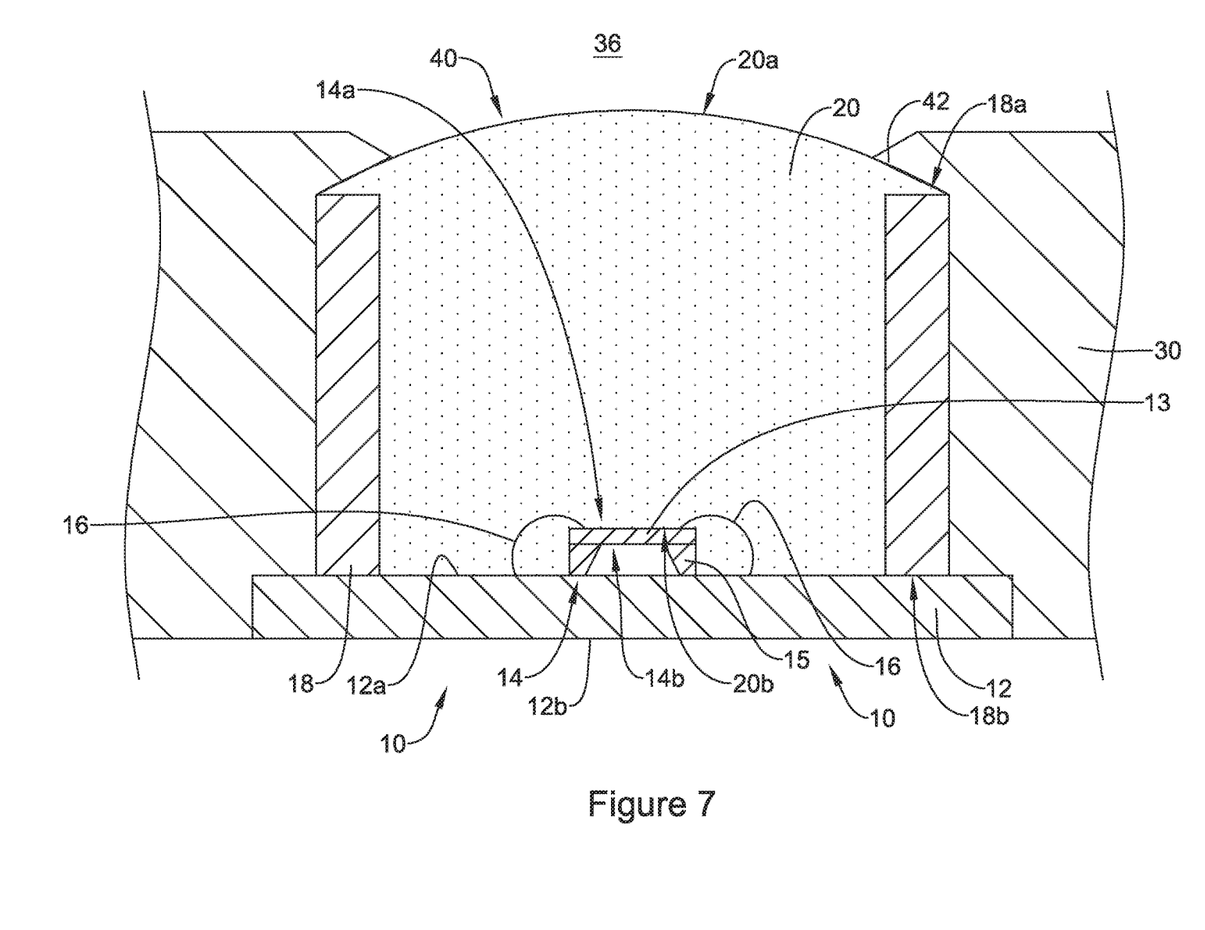
FIG. 7 is a schematic blown up view of circle 6 shown in FIG. 5.
Figure 8:
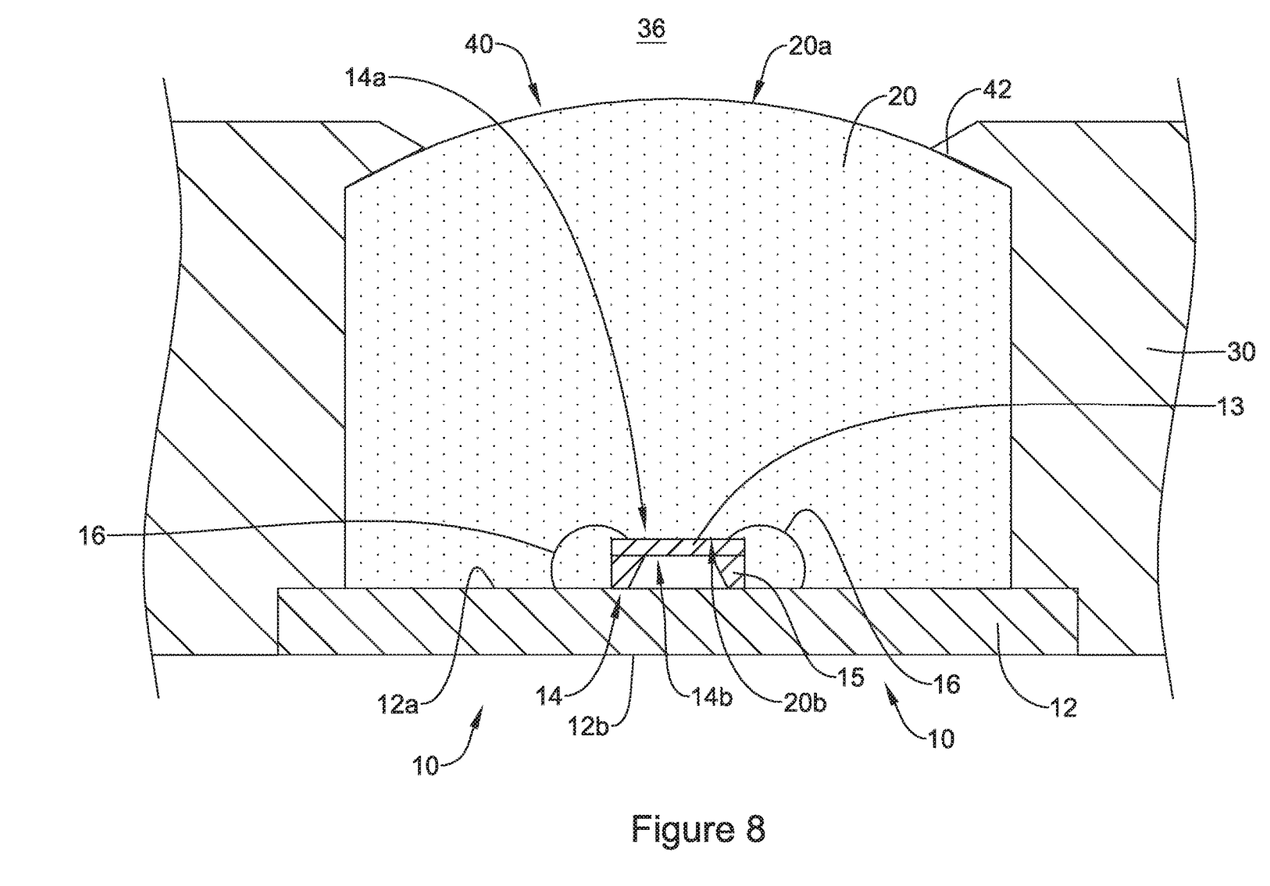
FIG. 8 is a schematic blown up view of circle 6 shown in FIG. 5 with another illustrative force transmitting member.

FIGS. 7 and 8 are magnified views of the interior of circle 6 shown in FIG. 6 with different pressure sensor assembly 10 configurations inserted into a wall of the reservoir 30. FIG. 7 depicts a configuration of the pressure sensor assembly 10 having a gel ring 18 around the force transmitting member 20. FIG. 8 depicts a configuration of the pressure sensor assembly 10 without a gel ring 18 around the force transmitting member 20.

In FIGS. 7 and 8, the pressure sensor assembly 10 is shown inserted into the opening 40 of the reservoir 30 such that the first side 20a of the force transmitting member 20 is exposed to the interior 36 of the reservoir 30. In operation, fluid pressure within the interior 36 of the reservoir 30 may push or apply a pressure to the first side 20a of the force transmitting member 20 and the pressure acting on the first side 20a of the force transmitting member 20 may be transferred to the second side 20b of the force transmitting member 20 and thus to the pressure sensor 14. The force (e.g. pressure) applied to the pressure sensor 14 may be converted into an electrical signal and transferred from the pressure sensor 14 to the PCB 12 (e.g., via wire bonds 16 or other electrical connection) and onto a pump processor (e.g., a microprocessor or other processor, not shown). In some cases, the electrical signal from the pressure sensor 14 may be transmitted to the pump processor via a connector that mechanically and electrically engages pads on the PCB 12 (e.g., pads on one or more of the first side 12a and the second side 12b of the PCB 12). When so configured, the pressure sensor assembly 10 may be configured to directly sense a pressure within the interior 36 of the reservoir and the processor of the pump may be configured to identify an occlusion event separate from other mechanical failures of the pump or system.

In some cases, the reservoir 30 may include a feature defining the opening 40 that is configured to engage the pressure sensor assembly 10 to form a seal between the pressure sensor assembly 10 and the reservoir 30. As shown in FIG. 7, the reservoir 30 may include one or more extensions 42 that define the opening 40 and are configured to engage the first side 20a of the force transmitting member 20 to form a seal between the reservoir 30 and the pressure sensor assembly 10. In the examples of FIGS. 7 and 8, the extensions 42 may have an outermost edge having two angled surfaces at least partially defining the opening 40. One angled surface of the outermost edge of the extensions 42 may extend circumferentially around the opening 40 and may facilitate engaging a domed or other shaped structure of the force transmitting member 20 to form a seal as the first side of the dome or other shape may be angled along an angled edge of the first side 20a of the force transmitting member 20. Further, the other angled surface located at the outermost edge of the extension 42 and facing the interior 36 of the reservoir 30 may facilitate directing fluid in the reservoir 30 to the outlet 38 of the reservoir 30 and reducing trapping fluid at the opening 40. The domed or other shape of the first side 20a of the force transmitting member 20 may be configured to help reduce the amount of fluid that is in the opening 40. Some medicines can be very expensive, and reducing the amount of medicine that is trapped in the opening 40 can have benefits.

The angled surfaces of the outermost edge of the extension 42 and/or the opening 40 may take on one or more configurations other than what is shown in FIGS. 7 and 8. For example, manufacturability and/or creating a seal between the pressure sensor assembly 10 and the reservoir 30, among other considerations, may be considered when configuring the extensions 42 and/or the opening 40.

Figure 9:
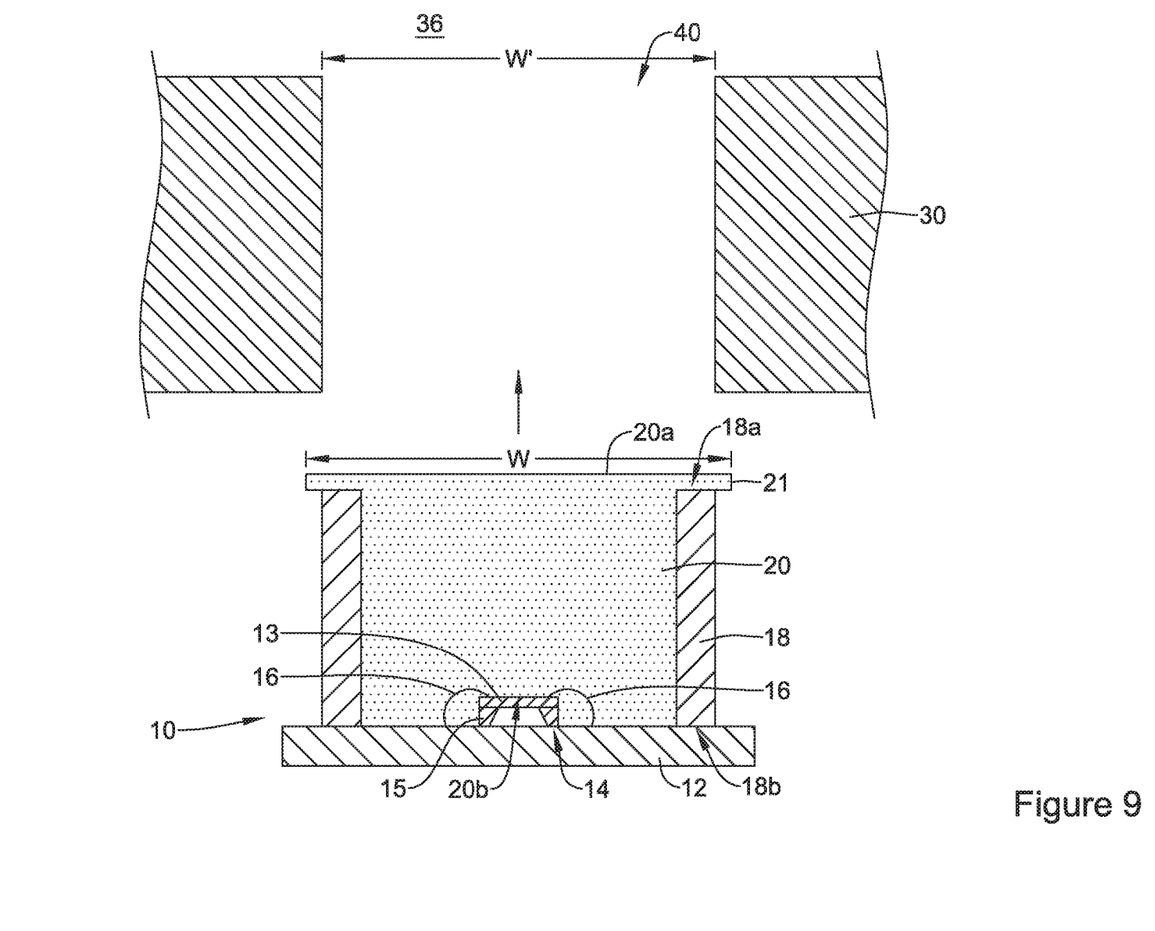
FIG. 9 is a schematic cross-section view of another illustrative pressure sensor assembly to be inserted into an opening of a reservoir.
Figure 10:
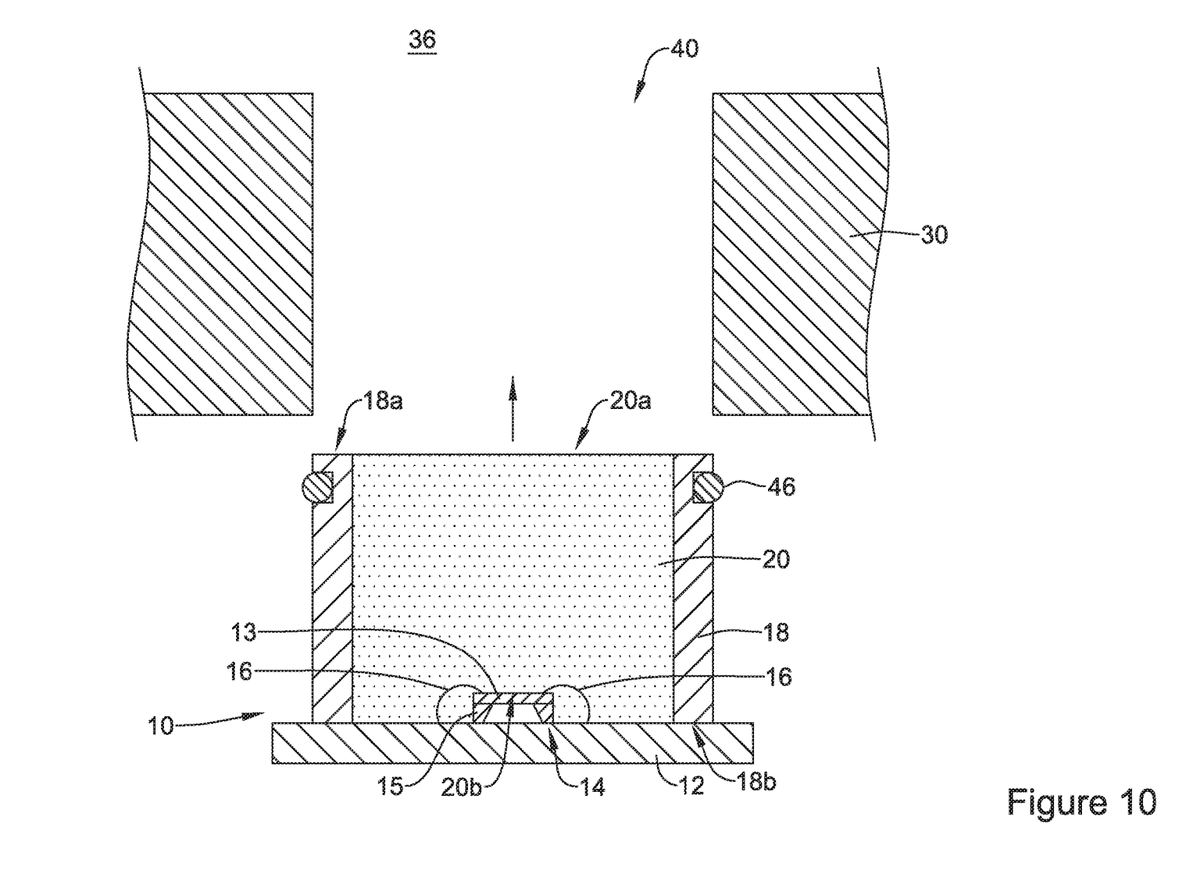
FIG. 10 is a schematic cross-section view of another illustrative pressure sensor assembly to be inserted into an opening of a reservoir.

FIGS. 9 and 10 depict different illustrative embodiments of the pressure sensor assembly 10 being inserted into an opening 40 of a reservoir 30. Although FIGS. 9 and 10 do not depict the extensions 42 defining the opening 40, the extensions 42 may be utilized to facilitate aligning the pressure sensor assembly 10 with an interior edge of the opening 40, but this is not required.

As is depicted in FIG. 9, a portion 21 of the force transmitting member 20 may overlap the first end 18a of the support ring 18 and/or extend radially outward from the support ring 18 and may have a width W. In some cases, the width W may be slightly wider than a diameter or width W' of the opening 40 in the reservoir 30, such that as the pressure sensor assembly 10 is inserted into the opening 40, the portion 21 of the force transmitting member 20 overlapping and/or extending radially outward from the support ring 18 may engage walls of the opening 40 and create a seal to seal the opening 40.

In operation, the pressure sensor assembly 10 may be advanced into the opening 40 until the first side 20a of the force transmitting member 20 is in-line or substantially in-line (e.g., where a dome, if present, of the force transmitting member 20 crosses or a portion of the force transmitting member 20 crosses) a surface of the reservoir 30 defining the interior 36 or to a different location along the opening 40. Positioning the first side 20a of the force transmitting member 20 in-line or substantially in-line with the interior surface of the reservoir may mitigate an amount of fluid that is trapped within the reservoir 30 around the pressure sensor assembly 10. Further, when extensions (e.g., extensions 42) are utilized for defining the opening 40, the force transmitting member 20 may include cut-outs or may be molded or otherwise configured to receive the extensions while allowing the first surface 20a of the force transmitting member 20 to be positioned at a desired location with respect to the interior 36 of the reservoir 30.

The portion 21 of the force transmitting member 20 that is configured to overlap and/or radially extend outward from the support ring 18 may be formed in one or more manners. In one example, a particular shape of the portion 21 of the force transmitting member 20 may be formed by a shape of a mold used to particularly shape and/or cure the force transmitting member 20. When some molding processes are used, the force transmitting member 20 may include flash that results from material leaking between two molds. This flash may be removed or left in place, as desired. In some cases, the portion 21 of the force transmitting member 20 may be created through deposit techniques (e.g., through a deposit technique when creating a dome of the force transmitting member 20) and/or one or more other techniques.

In addition to or as an alternative to the portion 21 of the force transmitting member 20 configured to overlap and/or extend radially outward from the support ring 18, the pressure sensor assembly 10 (as shown in FIG. 10) or the opening 40 may include an o-ring 46 configured to engage the support ring 18 and the wall of the opening 40. The o-ring 46 may be configured to engage the support ring 18 and/or other portion of the pressure sensor assembly 10 at any location along an exterior thereof. In some cases, it may be advantageous to have the o-ring 46 engage the support ring 18 and/or other portion of the pressure sensor assembly 10 at a location adjacent the interior 36 of the reservoir 30 to limit or mitigate an amount of fluid within the reservoir 30 that may become trapped at the pressure sensor assembly 10 (e.g., between the pressure sensor assembly 10 and the opening 40). In one example, as shown in FIG. 10, the o-ring 46 may be located and may engage the support ring 18 of the pressure sensor assembly 10 at a position adjacent the first end 18a of the support ring. In this example, when the pressure sensor assembly is inserted into the opening 40, the o-ring 46 may create a seal between the pressure sensor assembly 10 at a position adjacent the interior 36 of the reservoir 30.

In addition to, or as an alternative to, utilizing the o-ring 46 and/or the portion 21 of the force transmitting member 20, a gasket, an adhesive joint, or other type of seal may be used to create a seal between the pressure sensor assembly 10 and the opening 40 of the reservoir 30. These are just some examples.

Figure 11:
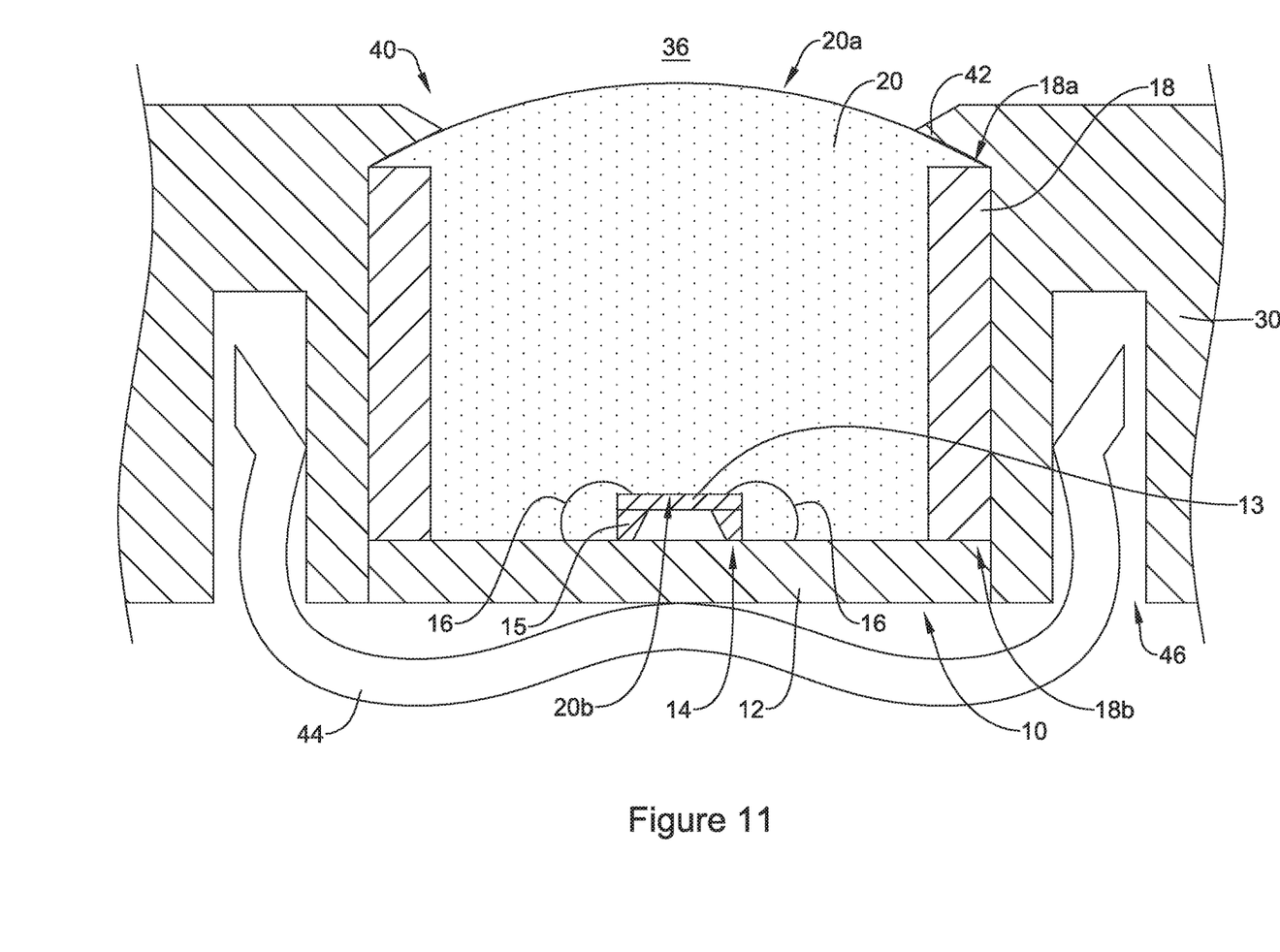
FIG. 11 is a schematic cross-section view of an illustrative pressure sensor assembly within a reservoir secured via a clip.

FIG. 11 depicts a clip 44 (e.g., a resilient clip) configured to secure the pressure sensor assembly 10 within the opening 40 of the reservoir 30. Once the pressure sensor assembly 10 has been inserted into the opening 40, and in some cases, the clip 44 may be applied to the pressure sensor assembly 10 and the reservoir 30 to secure the pressure sensor assembly 10 within the opening 40. In the example of FIG. 11, the clip 44 may apply a force on the PCB 12 of the pressure sensor assembly 10 and push the pressure sensor assembly 10 against the extension 42 or other portion of the reservoir 30 defining the opening 40. In the example shown, ends of the clip 44 may extend into one or more openings 40 defined in an exterior surface of the reservoir to secure the clip 44 to the reservoir. In some cases, the clip 44 may be formed from a metallic material. In some cases, the clip 44 may conduct electrical signals from the PCB 12 to an electrical contact in the reservoir 30 or the pump to facilitate sending pressure readings from the pressure sensor assembly 10 to the processor of the pump. Alternatively or in addition, the clip 44 may be formed from a polymer and/or one or more other materials.

Although FIG. 11 depicts the clip 44 as an M-shaped clip, the clip 44 may be any type of clip configured to secure (e.g., permanently or removably secure) the pressure sensor assembly 10 within the opening 40 and to the reservoir 30. Further, one or more other mechanisms may be utilized for securing the pressure sensor assembly 10 to the reservoir 30 including, but not limited to, adhesives, a cover, a threaded connection, a bayonet connection, and/or other securing technique.

Having thus described several illustrative embodiments of the present disclosure, those of skill in the art will readily appreciate that yet other embodiments may be made and used within the scope of the claims hereto attached. It will be understood that this disclosure is, in many respects, only illustrative. Changes may be made in details, particularly in matters of shape, size, and arrangement of parts without exceeding the scope of the disclosure. The disclosure's scope is, of course, defined in the language in which the appended claims are expressed.

What is claimed is:

1. A pressure sensor assembly comprising:
a printed circuit board having a front side and a back side;
a pressure sensor having a front side and a back side, the pressure sensor mounted to the printed circuit board with the back side of the pressure sensor facing the front side of the printed circuit board;
a ring having a front side and a back side, wherein the ring is mounted to the printed circuit board with the back side of the ring facing the front side of the printed circuit board and the front side of the ring spaced away from the front side of the printed circuit board, the ring extending circumferentially around the pressure sensor and defining an opening from the front side of the ring to the pressure sensor;
a force transmitting member positioned at least partially within the opening of the ring, the force transmitting member having a front side and a back side, wherein the front side of the force transmitting member includes a biocompatible cured silicone elastomer and the back side of the force transmitting member engages the front side of the pressure sensor, wherein the force transmitting member transmits a force applied to the front side of the force transmitting member to the front side of the pressure sensor;
a reservoir includes one or more extensions that define an opening,
wherein the first side of the force transmitting member is exposed to the interior of the reservoir, and
wherein the one or more extensions are configured to engage the first side of the force transmitting member to seal the opening.

2. The pressure sensor assembly of claim 1, wherein the pressure sensor includes a pressure sense die.

3. The pressure sensor assembly of claim 1, wherein the pressure sensor includes a pressure sense die secured to a constraint.

4. The pressure sensor assembly of claim 1, wherein the ring has a circular cross-section.

5. The pressure sensor assembly of claim 1, wherein the biocompatible cured silicone elastomer extends beyond the front side of the ring.

6. The pressure sensor assembly of claim 1, wherein the force transmitting member comprises a first layer and a second layer, wherein the first layer includes a gel that engages the front side of the pressure sensor, and the second layer includes the biocompatible cured silicone elastomer that forms the front side of the force transmitting member.

7. The pressure sensor assembly of claim 6, wherein the gel includes a fluoro-silicone gel.

8. The pressure sensor assembly of claim 1, wherein the front side of the force transmitting member forms a dome that extends away from the pressure sensor.

9. The pressure sensor assembly of claim 1, wherein the biocompatible cured silicone elastomer extends from the front side of the force transmitting member to the back side of the force transmitting member.

10. The pressure sensor assembly of claim 1, further comprising one or more wire bonds connecting one or more bond pads of the pressure sensor with one or more bond pads of the printed circuit board, wherein the ring extends circumferentially around the pressure sensor and the one or more wire bonds.

11. The pressure sensor assembly of claim 10, wherein the force transmitting member comprises a material that is cured within the ring and over the pressure sensor and the one or more wire bonds.

12. A pressure sensor assembly comprising:
a printed circuit board having a front side and a back side;
a pressure sensor having a front side and a back side, the pressure sensor mounted to the printed circuit board with the back side of the pressure sensor facing the front side of the printed circuit board; and
a force transmitting member having a front side and the back side, wherein the front side of the force transmitting member includes a cured elastomeric force transmitting member, and the back side of the force transmitting member engages the front side of the pressure sensor, and
wherein the force transmitting member transmits a force applied to the front side of the force transmitting member to the front side of the pressure sensor; and
a reservoir includes one or more extensions that define an opening,
wherein the first side of the force transmitting member is exposed to the interior of the reservoir, and
wherein the one or more extensions are configured to engage the first side of the force transmitting member to seal the opening.

13. The pressure sensor assembly of claim 12, wherein the front side of the force transmitting member forms a dome.

14. The pressure sensor assembly of claim 12, wherein the force transmitting member is configured to engage a reservoir and seal an opening in the reservoir.

15. The pressure sensor assembly of claim 12, further comprising a ring extending circumferentially around the pressure sensor and defining an opening from a front side of the ring to the pressure sensor, wherein at least part of the force transmitting member is positioned within the opening of the ring.

16. The pressure sensor assembly of claim 12, wherein the cured elastomeric force transmitting member is a biocompatible cured silicone elastomer.

17. The pressure sensor assembly of claim 12, wherein the pressure sensor includes a pressure sense die.

18. The pressure sensor assembly of claim 12, wherein the force transmitting member comprises a first layer and a second layer, wherein the first layer includes a gel that engages the front side of the pressure sensor, and the second layer includes the cured elastomeric force transmitting member that forms the front side of the force transmitting member.

19. The pressure sensor assembly of claim 18, wherein the gel includes a fluoro-silicone gel.

20. The pressure sensor assembly of claim 12, further comprising one or more wire bonds connecting one or more bond pads of the pressure sensor with one or more bond pads of the printed circuit board.

* * * * *